United States Patent [19]
Ukawa et al.

[11] Patent Number: 5,485,838
[45] Date of Patent: Jan. 23, 1996

[54] NON-INVASIVE BLOOD PRESSURE MEASUREMENT DEVICE

[75] Inventors: Teiji Ukawa; Tatsuo Yoshida, both of Tokyo, Japan

[73] Assignee: Nihon Kohden Corporation, Tokyo, Japan

[21] Appl. No.: 162,254

[22] Filed: Dec. 7, 1993

[30] Foreign Application Priority Data

Dec. 7, 1992 [JP] Japan ................................ 4-326632
Dec. 7, 1992 [JP] Japan ................................ 4-326633

[51] Int. Cl.$^6$ ........................................... A61B 5/00
[52] U.S. Cl. ..................... 128/633; 128/667; 128/677; 128/682; 128/687; 128/680; 128/670; 356/41
[58] Field of Search ........................... 128/633–634, 128/664–667, 670, 680, 681, 677, 672, 668; 356/41

[56] References Cited

U.S. PATENT DOCUMENTS

| | | | |
|---|---|---|---|
| 3,412,729 | 11/1968 | Smith, Jr. ........................ | 128/667 |
| 4,776,339 | 10/1988 | Schreiber ........................ | 128/670 |
| 4,780,824 | 10/1988 | Niwa et al. ..................... | 128/667 |
| 5,048,533 | 9/1991 | Muz ................................. | 128/679 |
| 5,111,817 | 5/1992 | Clark et al. .................... | 128/667 |
| 5,309,908 | 5/1994 | Friedman et al. ............... | 128/667 |

OTHER PUBLICATIONS

"Japanese Journal of Clinical Monitoring," vol. 13, No. 1, pp. 75–84, published Jan. 20, 1992.

*Primary Examiner*—Lee S. Cohen
*Assistant Examiner*—Robert L. Nasser, Jr.
*Attorney, Agent, or Firm*—Sughrue, Mion, Zinn, Macpeak & Seas

[57] ABSTRACT

A non-invasive blood pressure measurment device including: a cuff, a pressure detector for detecting a cuff pressure; a cuff pressure control pump for linearly increasing or decreasing the cuff pressure; a light-emitting member for injecting a beam of light into a part of a body by the cuff; light-receiving members for detecting an amount of light transmitted or an amount of light reflected of the beam of light injected into the body from the light-emitting member; a demodulating circuit for separating a pulsatile component from the light-receiving signal obtained from the light-receiving members; a CPU for sending a control signal to the cuff pressure control pump to thereby either increase the cuff pressure if it is judged that the pulsatile component has not been detected before applying pressure to the cuff based on the detection output from the demodulating circuit or decrease the once increased cuff pressure, and detecting an inflection point in the light-receiving signal in the course of increasing or decreasing the cuff pressure to thereby output a cuff pressure at the inflection point as a mean pressure value of a subject who is in systemic hypotension.

2 Claims, 10 Drawing Sheets

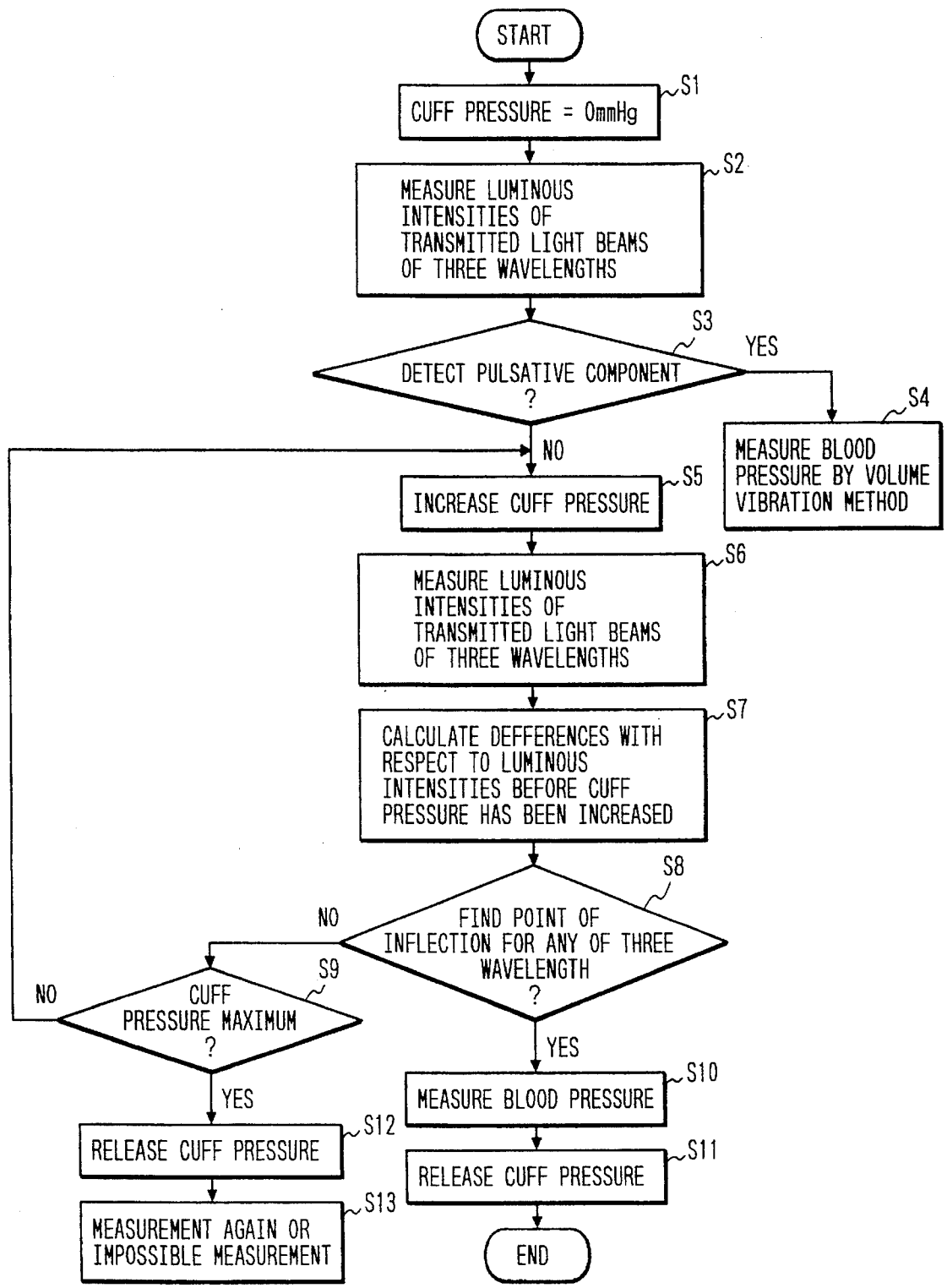

FIG. 10(a)
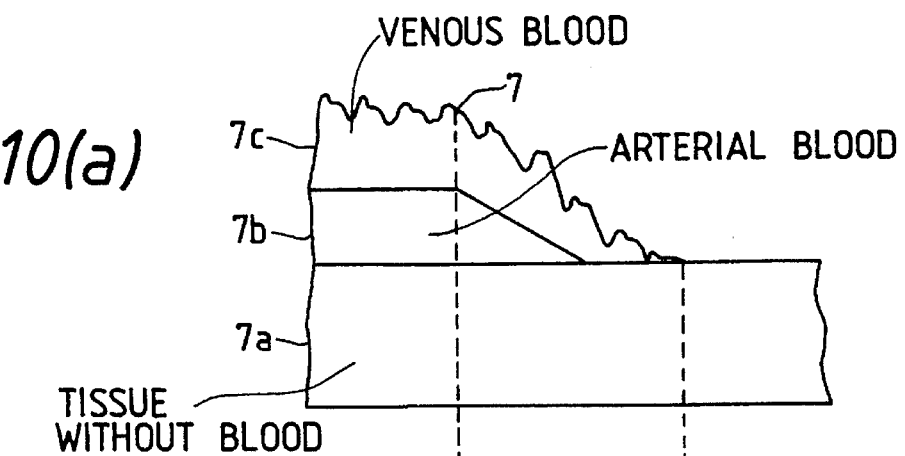
FIG. 10(b)
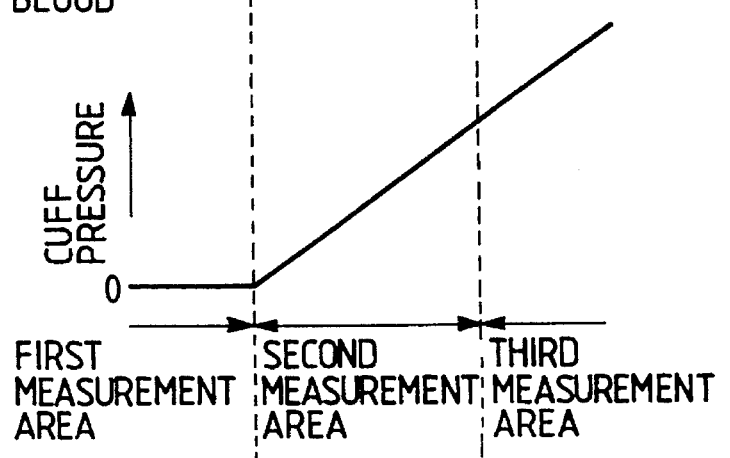
FIG. 10(c)
FIG. 10(d)
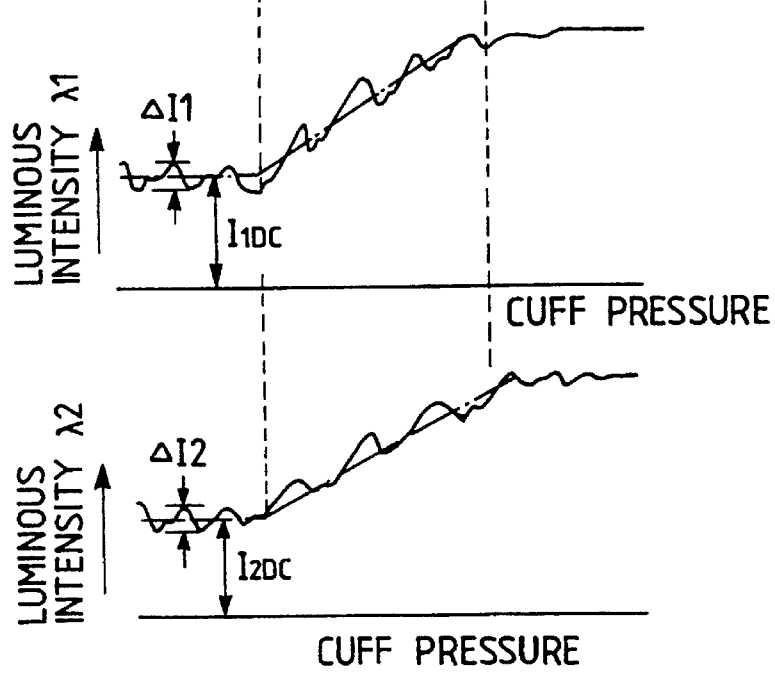

FIG. 12
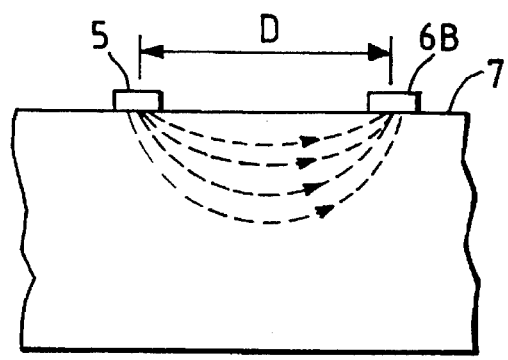
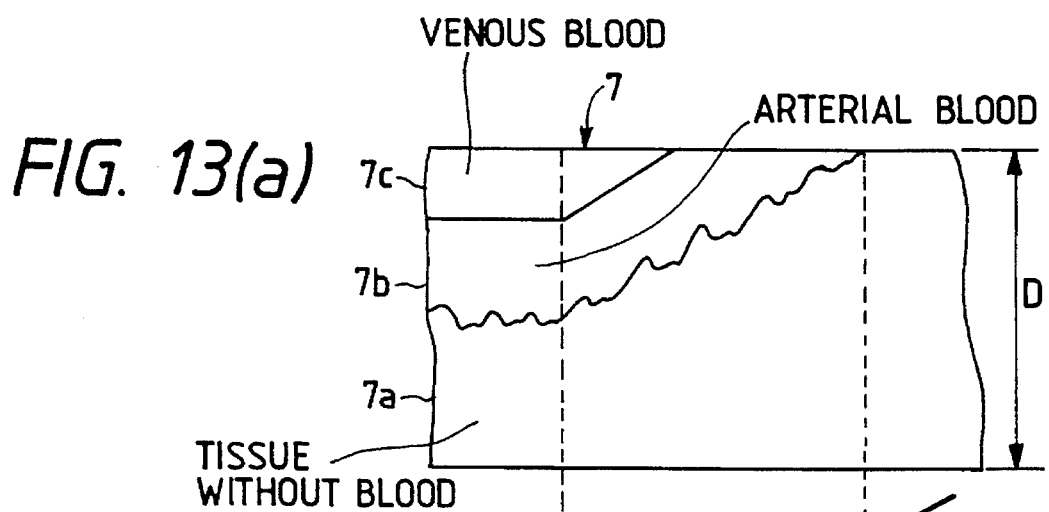
FIG. 13(a)
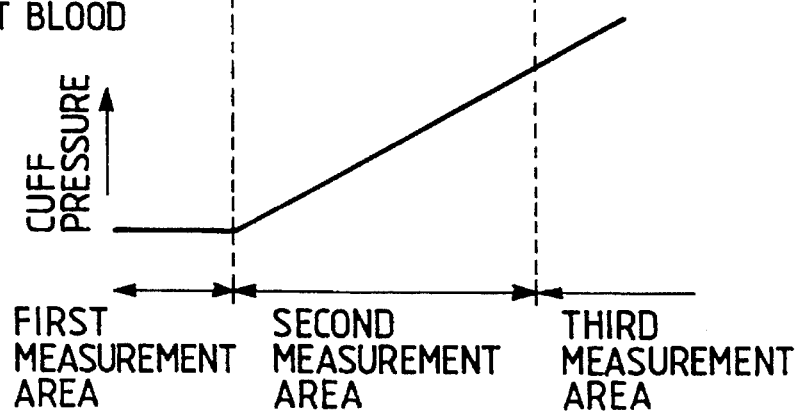
FIG. 13(b)

NON-INVASIVE BLOOD PRESSURE MEASUREMENT DEVICE

BACKGROUND OF THE INVENTION

1. Field of the Invention

This invention relates to a non-invasive blood pressure measurment device for measuring blood pressure of a subject in systemic hypotension and relates to a non-invasive blood pressure measurement device for measuring blood pressure of a subject by non-invasive means using a volume-oscillometric method. More particularly, the invention is directed to an improved non-invasive blood pressure measurement device that can correct measurement errors attributable to vibration based on the degree of variation in oxygen saturation measured simultaneously with the blood pressure.

2. Related Art

A photoelectric volume oscillometric method, for example, is known as a conventional method of measuring blood pressure of a subject by non-invasive means.

The photoelectric volume oscillometric method is designed to measure blood pressure by detecting a feeble change in vibration caused by blood pressure when the pressure of a cuff wrapped around a finger is increased or decreased. That is, this method detects a change in the volume of a blood vessel using a light-receiving element for receiving transmitted light from a light-emitting element, and measures blood pressure based on the cuff pressure and the amplitude of a photoelectric plethymograph signal that is an ac component of a light-receiving signal outputted from the light-receiving element. FIG. 7 shows a relationship between photoelectric cuff pressure and plethysmograph obtained when the cuff pressure is linearly increased. In the volume oscillometric method, a mean blood pressure value Pm can be calculated from a cuff pressure reading obtained when the plethysmograph has reached a maximum amplitude L, and a systolic blood pressure can be measured from a cuff pressure reading recorded when the plethysmograph has reached, e.g., 20% of the maximum amplitude L by further increasing the cuff pressure. Also, a diastolic blood pressure Pd can be calculated from a cuff pressure reading at an inflection point of an envelope of the plethysmograph observed in the course of increasing the cuff pressure from 0 mmHg.

A detail of non-invasive blood pressue measurement using such photoelectric volume oscillometric method is described in a periodical, "Japanese Journal of Clinical Monitoring" (Vol. 13, No. 1, 1990, pp. 75–84), published by the Clinical Monitor Society.

A non-invasive blood pressure measurement device that allows both blood pressure measurement by the volume oscillometric method and oxygen saturation measurement to be made simultaneously is proposed in Japanese Patent Unexamined Publication No. 2-305555.

Since this conventional non-invasive blood pressure measurement device based on the volume oscillometric method is designed to measure blood pressure by detecting a photoelectric volume pulse as described above, in the case where vibration is introduced from an external source when a subject is carried in an ambulance or in the case where noise attributable to movement of his body is picked up, measurement errors have resulted unavoidably.

By the way, when the subject is in shock due to ventricular fibrillation or in a low blood pressure state due to severe hemorage, the conventional non-invasive blood pressure measurement devices cannot provide blood pressure measurements in some cases.

To overcome this problem, an attempt has been made to obtain some kind of blood pressure information from the subject in shock or the like. That is, what is proposed is a non-invasive blood pressure measurement capable of determining that the subject is in systemic hypotension, which is less than 60 mmHg (or in pulsational arrest), by checking if a plethysmograph is detected while observing a plethysmograph signal from the light-receiving element under the cuff pressure set to a predetermined value, e.g., to 60 mmHg.

However, the blood pressure measurement under a cuff pressure of a predetermined value such as 60 mmHg permits a determination of the systemic hypotension of a subject around such predetermined blood pressure value. The blood pressure of a subject in shock cannot be measured by this method.

Amid demands for quick emergency medical treatment, it is of importance that blood pressure be measured immediately after a subject in shock or the like has been carried in the ambulance so that emergency medical treatment can be given him thereafter.

SUMMARY OF THE INVENTION

The invention has been made to overcome these problems encountered by the conventional art. Accordingly, an object of the invention is to provide a non-invasive blood pressure measurement device capable not only of judging whether or not a subject is in systemic hypotension but also of measuring the blood pressure of such subject in systemic hypotension with ease.

Another object of the invention is to provide a non-invasive blood pressure measurement device capable of measuring blood pressure by controlling errors even if noise due to vibration or movement of the body is picked up.

To achieve the above objects, a first aspect of the invention is applied to a non-invasive blood pressure measurement device, which includes: a cuff for being attached to a part of a body of a subject; a pressure detector for detecting a cuff pressure applied to the subject by the cuff; a pressure applying means for either applying pressure to the cuff by an inputted pressure increase control signal or dropping the cuff pressure by inputting a pressure decrease control signal; a light-emitting section for injecting a beam of light onto the part of the body to which pressure is applied by the cuff; a light-receiving section for detecting an amount of light transmitted or an amount of light reflected of the beam of light injected onto the body from the light-emitting section; a pulse wave detecting means for separating a pulsatile component from a light-receiving signal obtained from the light-receiving section; a cuff pressure control means for outputting the pressure increase control signal to the pressure applying means while receiving a detection output from the pressure detector when it is judged that the pulsatile component has not been detected before applying pressure to the cuff based on the detection output from the pulse wave detecting means, or outputting the pressure decrease control signal for dropping the once increased cuff pressure to the pressure applying means; and a blood pressure value measuring means for detecting an inflection point of the light-receiving signal in the course of increasing the cuff pressure or in the course of decreasing the cuff pressure by the cuff pressure control means and outputting the cuff pressure at the inflection point as a mean blood pressure value of the subject under the systemic hypotension in response to the detection output from the pressure detector.

The non-invasive blood pressure measurement device according to the invention is so designed that beams of light of a plurality of wavelengths can be emitted from the light-emitting section on a time-sharing basis; and that when an inflection point is found in either one of the light-receiving signals of the plurality of wavelengths, a cuff pressure at such inflection point is outputted as the mean blood pressure value.

A second aspect of the invention is applied to a non-invasive blood pressure measurement device, which includes: a cuff for being attached to a part of a body of a subject; a pressure detector for detecting a cuff pressure applied to the subject by the cuff; a pressure applying means for applying pressure to the cuff by an inputted pressure increase control signal, or dropping the cuff pressure by inputting a pressure decrease control signal; a light-emitting section for injecting beams of light of two different wavelengths, one being a beam of red light and the other being a beam of infrared light, onto the part of the body to which pressure is applied by the cuff; a light-receiving section for detecting amounts of light transmitted or amounts of light reflected of the beams of light injected onto the body from the light-emitting section; a signal component separating means for separating a dc component and a pulsatile component from light-receiving signals of the respective wavelengths obtained from the light-receiving section; an oxygen saturation calculating means for calculating a ratio of a pulsation component in absorption of one wavelength due to arterial blood flow to that of the other wavelength from the dc components and the pulsatile components of the respective wavelengths obtained from the signal component separating means, and calculating an oxygen saturation from the ratio; a permissible range of variance calculating means for obtaining a mean value of oxygen saturations of the subject before applying pressure to the cuff, and calculating a permissible range of variance from the mean value, the oxygen saturations being those obtained by the oxygen saturation calculating means; a cuff pressure control means for outputting the pressure increase control signal to the pressure applying means while receiving the detection output from the pressure detector, or outputting the pressure decease control signal for dropping the once increased cuff pressure to the pressure applying means after the permissible range of variance has been obtained; a judging means for judging whether or not an oxygen saturation obtained in the course of increasing or decreasing the cuff pressure is within the permissible range of variance; and a blood pressure measuring means for selecting a valid pulse wave signal from the pulse wave signals obtained by the signal component separating means in the course of increasing or decreasing the cuff pressure based on a result of the judgment by the judging means, and calculating a blood pressure value of the subject by a volume oscillometric method from an amplitude of the valid pulse wave signal and the cuff pressure value obtained by the pressure detector.

As described above, according to the first aspect of the invention, a subject in shock or exhibiting an extremely low blood pressure, for whom it is difficult to measure blood pressure by the conventional volume oscillometric method, can be subjected not only to judgment of whether or not he is in the systemic hypotension, but also to measure the blood pressue of the subject in the systemic hypotension. Therefore, the invention can make a great contribution to the improvement of clinical treatment, particularly, of emergency medical treatment.

Moreover, according to the second aspect of the invention, in a measuring environment involving vibration or movement of the body for which it is difficult to measure blood pressure by the conventional volume oscillometric method, reliable blood pressure measurement can be effected on a subject.

Accordingly, the invention can improve reliability of blood pressure measurment in ambulances, which have measurements heretofore imposed problems, thereby contributing to the improvement of emergency medical treatment.

BRIEF DESCRIPTION OF THE DRAWINGS

FIG. 2 is a flowchart showing an operation procedure of the sphygmomanometer of FIG. 1;

FIG. 10(a) is a schematic diagram of the tissue in the case of measuring blood pressure by detecting transmitted light;

FIG. 10(b) is a diagram showing increase in the cuff pressure during measurement;

FIG. 10(c) is a diagram showing a waveform of received light of a wavelength $\lambda 1$, the waveform being detected when such increase has occurred;

FIG. 10(d) is a diagram showing a waveform of the received light of a wavelength $\lambda 2$, the waveform being detected when such increase has taken place;

FIG. 12 is a diagram illustrative of how reflected light after its transmission through the tissue is received by the light-receiving section;

FIG. 13(a) is a schematic diagram of the tissue in the case of measuring blood pressure by detecting reflected light; and FIG. 13(b) is a diagram showing increase in the cuff pressure during measurement;

DETAILED DESCRIPTION OF THE PREFERRED EMBODIMENTS

The basic concept of a first embodiment of the invention will now be described.

It can be determined that a subject is in systemic hypotension pressure if no pulsatile component is found in a measured signal from the subject before applying pressure to a cuff.

Figure 3A:
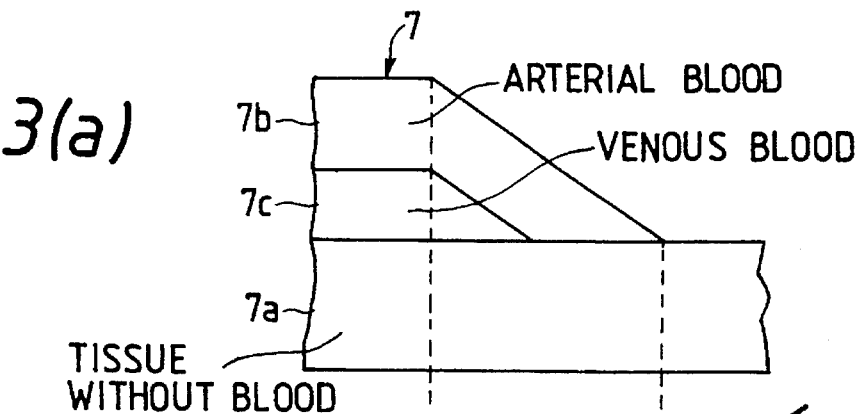
FIG. 3(a) is a schematic diagram of a tissue in the case of measuring blood pressure by detecting transmitted light.
Figure 3B:
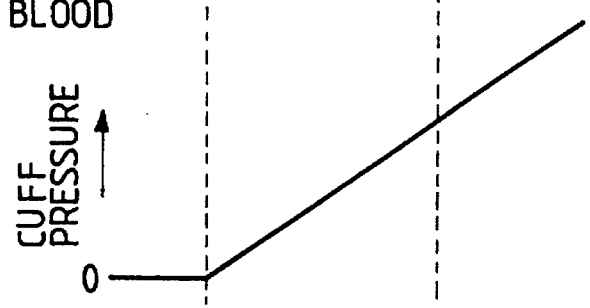
FIG. 3(b) is a diagram showing increase in a cuff pressure during measurement.
Figure 3C:
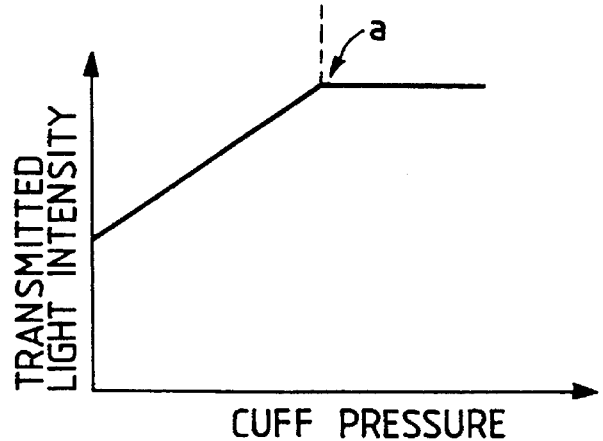
FIG. 3(c) is a diagram showing luminous intensity of a light-receiving signal detected when such increase has occurred.
Figure 4:
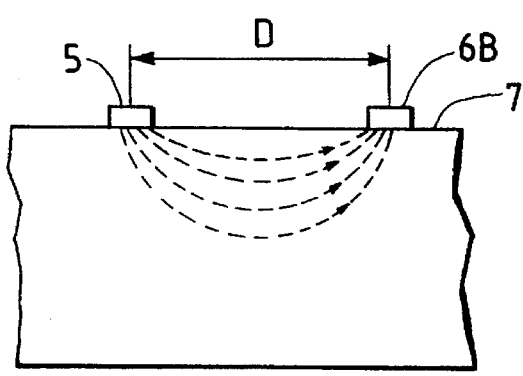
FIG. 4 is a diagram illustrative of how reflected light after its transmission through the tissue is received by a light-receiving section.

When pressure is applied to a part of the body of a subject who is in systemic hypotension, e.g., to a finger of his hand, by a cuff 4 that increases the cuff pressure linearly as shown in FIG. 3(b), the thickness of a tissue portion 7a of a tissue 7 is maintained constant, whereas arterial blood 7b and venous blood 7c thereof are gradually eliminated as shown in FIG. 3(a). The tissue 7 is interposed between a light-emitting section 5 and a light-receiving section 6A (see FIG. 1), and the tissue portion 7a does not contain blood. As a result, the luminous intensity of transmitted light detected at the light-emitting section 6A gradually increases due to a decrease in light-extinguishing elements (the arterial blood and the venous blood) associated with an increase in the cuff pressure, making the cuff pressure larger than the arterial blood pressure. When all the blood has been eliminated, leaving only the tissue portion 7a, change in the luminous intensity settles at a substantially constant level. At a timing when all the arterial blood has been eliminated completely, a drastic change is observed in the inclination of the luminous intensity as shown in FIG. 3(c). If such timing is detected as an inflection point a and if the cuff pressure is read at this inflection point a, then a mean blood pressure value of the subject who is in systemic hypotension can be measured.

On the other hand, if the cuff 4 is attached to a brachial arm of the subject, the transmitted light cannot be detected. Therefore, the light-emitting section 5 and a light-receiving section 6B are arranged on the same plane so as to be equidistantly apart from each other, so that reflected light is detected by the light-receiving section 6B after a beam of light emitted from the light-emitting section 5 has been extinguished by its transmission through the tissue 7.

Figure 5A:
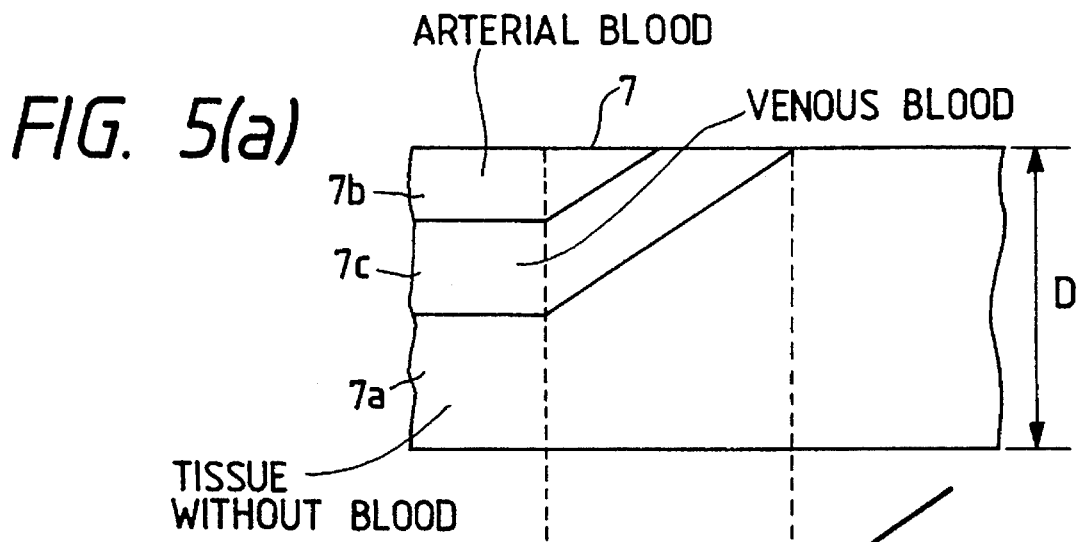
FIG. 5(a) is a schematic diagram showing the tissue in the case of measuring blood pressure by detecting reflected light.
Figure 5B:
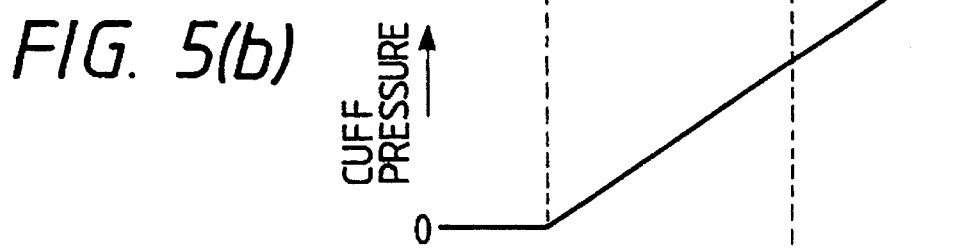
FIG. 5(b) is a diagram showing increase in the cuff pressure during measurement.
Figure 5C:
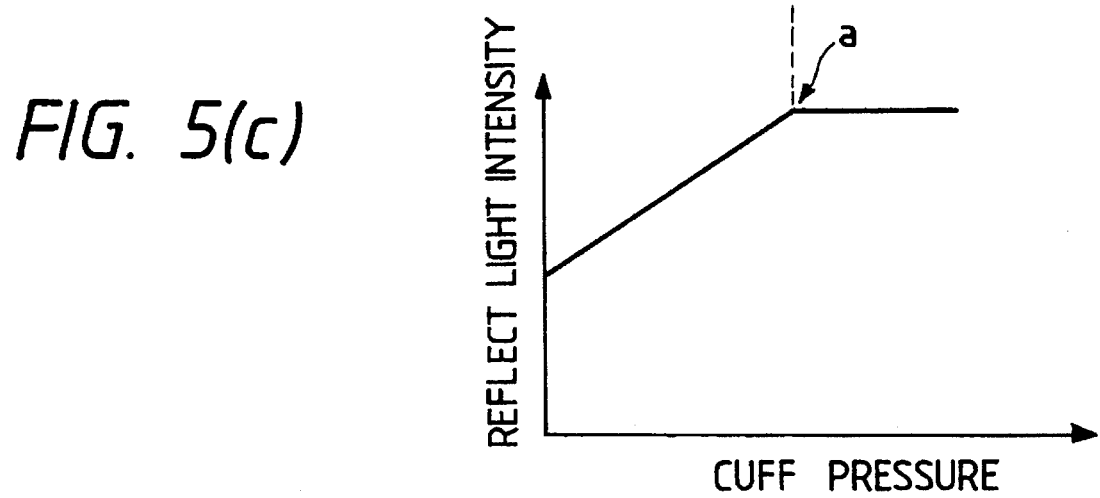
FIG. 5(c) is a diagram showing luminous intensity of a light-receiving signal detected when such increase has occurred.

In this case, if the cuff pressure is linearly increased as shown in FIG. 5(b) after the subject has been judged to be in systemic hypotension, then an optical path length D, which is a distance between the light-emitting section 5 and the light-receiving section 6B can be maintained constant. However, since the arterial blood 7b and the venous blood 7c are being gradually eliminated, the luminous intensity of the reflected light detected by the light-receiving section 6B gradually increases. When the cuff pressure has exceeded the arterial blood pressure, all the blood is removed to leave only the tissue portion 7a. As a result, the inclination of the luminous intensity of the reflected light changes drastically as shown in FIG. 5(c), and the change with respect to the cuff pressure becomes extremely small thereafter. If an inflection point a is detected and if the cuff pressure is read at such point, a mean blood pressure value of the subject who is in systemic hypotension can be measured.

Figure 6:
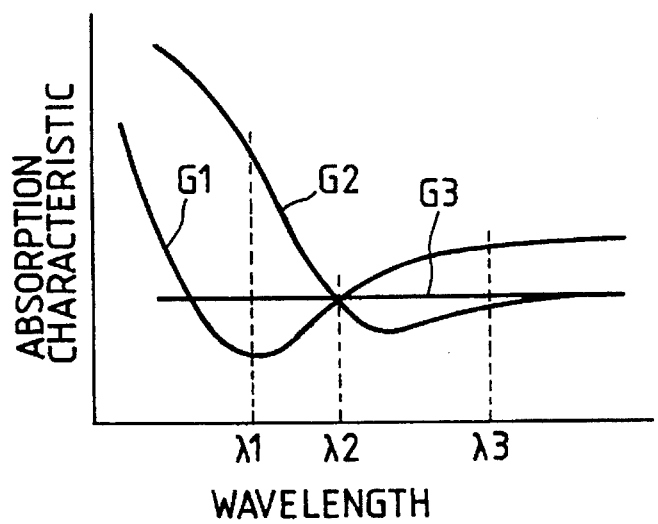
FIG. 6 is a characteristic diagram illustrative of an example in which absorption of tissue, arterial blood, and venous blood coincide with one another, by wavelength.
Figure 7:
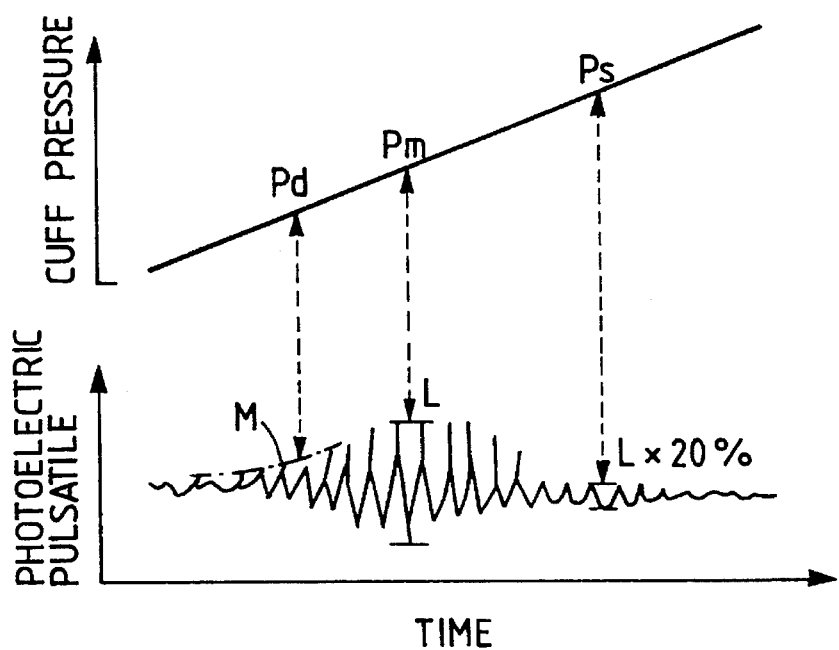
FIG. 7 is a diagram showing a relationship between cuff pressure and amplitude of a plethysmograph in a volume oscillometric method.

By the way, there exists a wavelength at which all the tissue portion 7a not containing blood, the arterial blood 7b, and the venous blood 7c exhibit the same absorption characteristic. FIG. 6 shows an example in which an absorption characteristic G3 of the tissue portion, an absorption characteristic G1 of the arterial blood, and an absorption characteristic G2 of the venous blood coincide with one another at the absorption wavelength λ2, out of three wavelengths λ1, λ2, λ3. Blood pressure measurement using a wavelength at which the absorption of the tissue portion, the arterial blood, and the venous blood coincide with one another is difficult, especially when the measurement involves light reception of the reflected light, because the optical path length is inconstant regardless of the fact that the arterial blood and the venous blood are eliminated from the tissue.

To overcome this problem, if it is so arranged that beams of light of a plurality of wavelengths, e.g., three wavelengths, can be sequentially emitted from the light-emitting section 5, there is no likelihood that the absorption characteristics of all the wavelengths will coincide with one another. Therefore, such arrangement allows not only judgment of whether or not a subject is in systemic hypotension but also, if it has been determined that the subject is under the systemic hypotension, measurement of a mean blood pressure value using any one of the plurality of wavelengths.

Further, in measurements involving the detection of transmitted light, the use of a plurality of wavelengths ensures reliable and accurate measurement.

A non-invasive blood pressure measurement device, which is a first embodiment of the invention, will now be described in detail with reference to the accompanying drawings.

Figure 1:
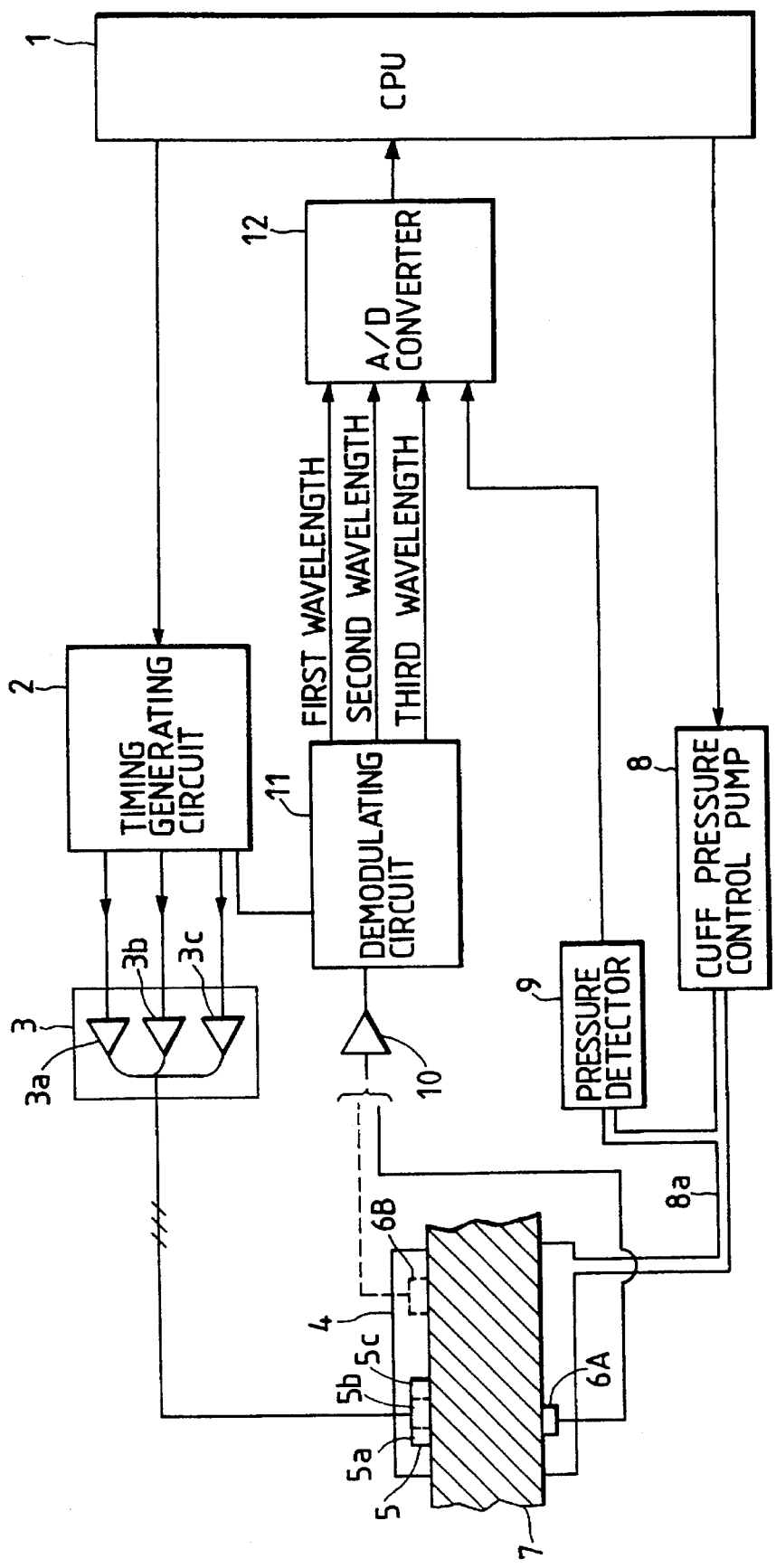
FIG. 1 is a block diagram showing a non-invasive blood pressure measurement device, which is a first embodiment of the invention.

The sphygmomanometer, which is the first embodiment, is shown by a block diagram in FIG. 1. In FIG. 1, a light-emitting section 5 and a light-receiving section 6A are mounted on the inner surface of a cuff 4 so as to be integral with the cuff 4, which is attached to a part of the body of a subject, e.g., a finger of his hand. The light-emitting section 5 is used to inject beams of light onto a tissue 7 of the subject, and the light-receiving section 6A is disposed on a side opposite to the light-emitting section 5 so that the tissue 7 is interposed therebetween. Here, it is assumed that the tissue 7 includes: a tissue portion 7a not containing blood; arterial blood 7b, and venous blood 7c (see FIG. 3(a)). The light-receiving section 5 is formed of light-emitting elements that emit beams of light of three different wavelengths, such as three light-emitting diodes 5a, 5b, 5c. Emitted from the respective light emitting diodes 5a, 5b, 5c are a beam of light with a first wavelength of 660 nm, a beam of light with a second wavelength of 805 nm, and a beam of light with a third wavelength of 940 nm. Instead of using the three light-emitting diodes, filters of the respective colors disposed in front of light sources may be switched to emit beams of light of three wavelengths. The light-receiving section 6A is formed of a light-receiving element such as a phototransistor, and detects the amounts of light transmitted after the beams of light injected from the light-emitting section 5 have been transmitted through the tissue 7.

The cuff 4 is connected to a cuff pressure control pump 8 through an air tube 8a, the pump 8 including a drive circuit. The operation of increasing, decreasing, or releasing the cuff pressure can be performed by inputting a control signal from a central processing unit (CPU) 1 to the pump 8 that serves as a pressure applying means.

The pressure to be applied to the tissue 7 by the cuff 4 is detected by a pressure detector 9, and the output of the pressure detector 9 is received by the CPU 1 after being converted into a digital signal by an A/D converter 12.

A timing generating circuit 2 under control of the CPU 1 applies not only pulse signals to buffers 3a, 3b, 3c of a driver circuit 3, but also timing signals to a demodulating circuit 11. The pulse signals determine timings for sequentially driving the respective light-emitting diodes 5a, 5b, 5c on a time-sharing basis. The timing signals serve to separate light-receiving signals from the output signals of the light-receiving section 6A at every wavelength.

The respective buffers 3a, 3b, 3c sequentially amplify the received pulse signals and drive the respective light-emitting diodes 5a, 5b, 5c. Accordingly, the light-emitting diodes 5a, 5b, 5c sequentially inject beams of light with the first into the third wavelengths to the tissue 7.

The light-receiving section 6A detects the amounts of light transmitted after the beams of light injected from the light-emitting diodes 5a, 5b, 5c have been extinguished by their transmission through the tissue 7. These light-receiving signals are supplied to the demodulating circuit 11 after being amplified by an input amplifier 10.

The demodulating circuit 11 not only separates light-receiving signals at every wavelength from its input signals based on the timing signals, but also separates a dc component and a pulsatile component from each light-receiving signal. The signal components outputted from the demodulating circuit 11 are received by the CPU 1 after being converted into digital signals.

Here, the demodulating circuit 11 constitutes a pulse wave detecting means, and the CPU 1 constitutes a cuff pressure controlling means and a blood pressure measuring means.

An operation of the thus constructed non-invasive blood pressure measurement device will be described with reference to a flowchart of FIG. 2.

At the measurement start timing, the cuff is not pressured; i.e., the cuff pressure is maintained at 0 mmHg (Step S1). Under this condition, the beams of light of the respective wavelengths are sequentially injected onto the tissue 7 from the light-emitting diodes 5a, 5b, 5c of the light-emitting section 5, and the amounts of light transmitted are detected by the light-receiving section 6A. From each signal outputted from the light-receiving section 6A are a dc component and a pulsatile component separated in the demodulating circuit 11, and these components are received by the CPU 1 (Step S2). The CPU 1 determines whether or not each light-receiving signal includes the pulsatile component (Step S3). If the pulsatile component has been detected, the CPU 1 performs a series of processing steps for measuring a mean blood pressure value Pm, a systolic blood pressure value Ps, and a diastolic blood pressure value Pd of the subject using photoelectric volume oscillometric method (Step S4).

On the other hand, if no pulsatile component has been detected, it is judged that the subject is in systemic hypotension. The CPU 1 outputs a pressure increase control signal to the cuff pressure control pump 8. Accordingly, the pressure of the cuff 4 is linearly increased by the pump 8 (Step S5). In the course of increasing the cuff pressure, the CPU 1 sequentially measures the luminous intensities of the transmitted light beams of the three wavelengths, and calculates differences with respect to the luminous intensities before the cuff pressure has been increased (Steps S6 and S7). The CPU 1 then determines whether or not an inflection point a at which the inclination of the luminous intensity of the transmitted light beam chagas drastically exists for any of the three wavelengths based on the calculated values. If no inflection point has been found, then the CPU 1 determines whether or not the cuff pressure has reached a set maximum value, e.g., 180 mmHg. If the maximum cuff pressure has not been reached, the processing is repeated from Step S5.

If the inflection point a has been found in Step S8 for any of the three wavelengths, then the cuff pressure at such inflection point a is detected and displayed as a mean blood pressure value (Step S10). At the same time, a cuff pressure release signal is sent to the cuff pressure control pump 8 to release the cuff pressure (Step S11).

If it is judged that the maximum cuff pressure has been reached in Step S9, then either the cuff pressure is measured again after releasing the cuff pressure or the processing to be performed when measurement is not possible is performed (Steps S12, S13).

More accurate measurement can be made if the processing for measuring the mean blood pressure value is performed again by sending a pressure decrease control signal from the CPU 1 to the cuff pressure control pump 8 and detecting the inflection point a even in the course of linearly decreasing the cuff pressure after the cuff pressure has reached the maximum blood pressure.

Then, a case where measurement is made by attaching the cuff 4 to a brachial arm of the subject will be described. In this case, the light-emitting section 5 and a light-receiving section 6B are linearly mounted on the inner surface of the cuff 4 so as to be apart from each other by a predetermined distance as shown by a broken line in FIG. 1. The predetermined distance is the optical path length D between the light-emitting section 5 and the light-receiving section 6B.

In this case, the respective light-emitting diodes 5a, 5b, 5c of the light-emitting section 5 sequentially inject beams of light with three different wavelengths into the tissue 7. The amounts of light reflected after the beams of light have been extinguished by their transmission through the tissue 7 are detected by the light-receiving section 6B. A measurement procedure in this case is as shown by the flowchart of FIG. 2.

While the light-emitting section 5 is formed of the three light-emitting diodes 5a, 5b, 5c that emit beams of light of different wavelengths in the above two cases, the number of wavelengths of light emitted from the light-emitting section 5 are not limited to three; e.g., the number of wavelengths may be two.

Particularly, when the measurement is made on a finger of a hand, it is the transmitted light, not the reflected light, that is detected. Therefore, the arrangement in which a beam of a single wavelength is emitted by the light-emitting section 5 may be acceptable.

As described above, according to the first embodiment of the invention, a subject in shock or exhibiting extremely low blood pressure, for whom it is difficult to measure blood pressure by the conventional volume oscillometric method, can be analyzed not only as to whether or not he is in the systemic hypotension, but also as to his actual blood pressue even if he is in systemic hypotension. Therefore, the invention can make a great contribution to the improvement of clinical treatment, particularly, of emergency medical treatment.

Second embodiment

The basic concept of a second embodiment of the invention will be described next. The parts which have been described with reference to the first embodiment are designated by the same reference numerals or charcters.

In the case where blood pressure is measured by wrapping the cuff 4 around a part of the body of a subject, e.g., a finger of his hand, the tissue 7 interposed between the light-emitting section 5 and the light-receiving section 6A (see FIG. 8) can be schematically illustrated as shown in FIG. 10(a). Here, reference character 7a designates a tissue portion not containing blood; 7b, arterial blood that pulsates; and 7c, venous blood.

When two wavelengths λ1, λ2 of red light and infrared light are injected from the light-emitting section 5 on a time-sharing basis, the light-receiving section 6A produces transmitted light outputs of wavelengths λ1, λ2 such as shown in FIGS. 10(c), (d). The luminous intensities of the transmitted light beams with these wavelengths are detected as a pulsatile component (ac component) $\Delta I_1 . \Delta I_2$ superposed on a dc component $I_{1DC} . I_{2DC}$. A pulsation component $\Delta A1$ in the absorption of the wavelength λ1 of the red light and a pulsation component $\Delta A2$ in the absorption of the wavelength λ2 of the infrared light can be calculated from the following equations.

$$\Delta A1 = \Delta I_1 / I_{1DC}$$

$$\Delta A2 = \Delta I_2 / I_{2DC}$$

A ratio Φ of the pulsation component in the absorption of the wavelength λ1 to the pulsation component in the absorption of the wavelength λ2 can be given by the following equation, using $\Delta A1$, $\Delta A2$.

$$\Phi = \Delta A1 / \Delta A2$$

The oxygen saturation S can be given as a function f of the absorption ratio Φ.

Figure 11A:
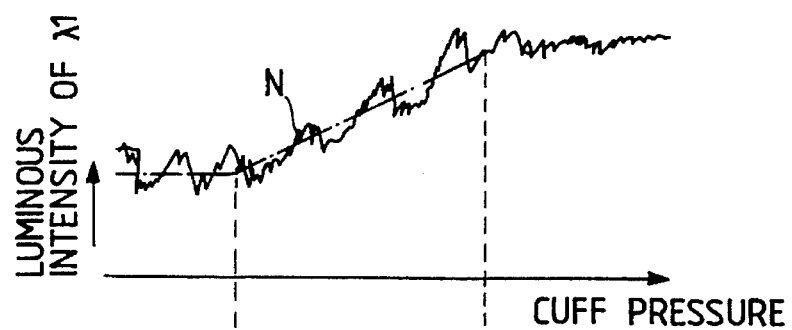
FIG. 11(a) is a diagram showing a waveform of received light of the wavelength $\lambda 1$ when noise has been picked up.
Figure 11B:
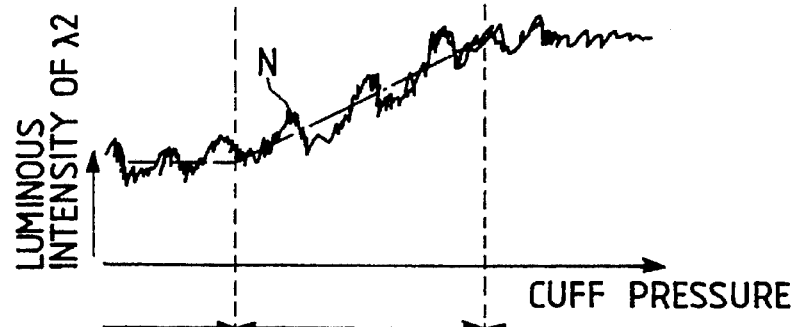
FIG. 11(b) is a diagram showing a waveform of the received light of the wavelength $\lambda 2$ when noise has been picked up.
Figure 11C:
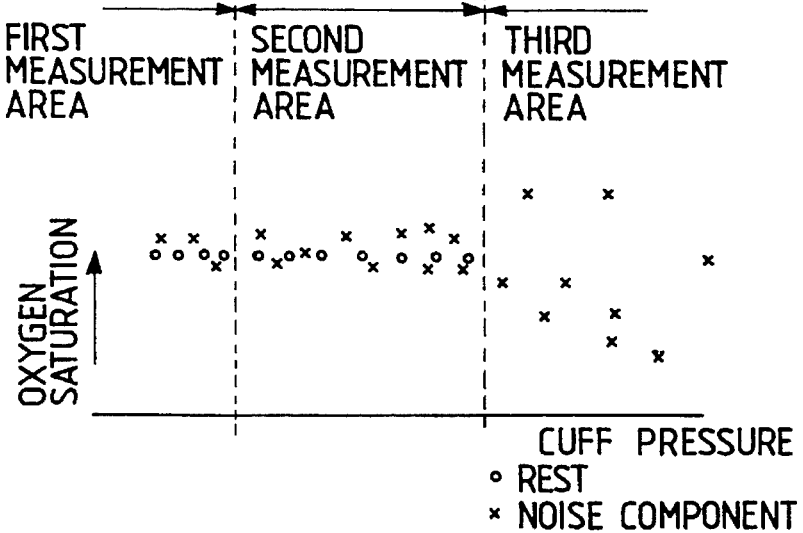
FIG. 11(c) is a diagram showing variation in oxygen saturation when noise has been picked up.

An oxygen saturation calculating means implemented by the CPU 1 measures the oxygen saturation S in a first measuring area, i.e., before the cuff pressure is applied, or when the cuff pressure is 0 mmHg. If noise due to vibration or movement of the body is introduced into the subject, then outputs of the transmitted light including a noise component N such as shown in FIGS. 11(a), (b) are detected at the light-receiving section 6A. Therefore, the oxygen saturations S measured when the noise component has been picked up (indicated by crosses) exhibit variation compared with those measured when the subject is at rest (indicated by circles) as shown in FIG. 11(c).

A permissible range of variance calculating means implemented by the CPU 1 calculates a mean value K of the oxygen saturations S having variations measured in the first measuring area, and multiplies K by an allowance (±A%), which is an appropriate coefficient A, to obtain a permissible range of variance δ. Here, the allowance is a value predetermined by a measurement environment in which the subject is placed, the measurement environment being, e.g., vibration the subject receives (e.g.) vibration received by the subject when the subject is carried in the ambulance). Any arbitrary value can be inputted to the CPU 1 from an external unit as the allowance.

Then, when the cuff pressure is increased linearly as shown in FIG. 10(b) by the pressure applying means that is under control of the cuff pressure control means implemented by the CPU 1, the finger of the hand of the subject is pressed by the cuff 4, which in turn gradually eliminates both the arterial blood 7b and the venous blood 7c that serve as the elements for extinguishing the light (see FIG. 10(a)). As a result, the luminous intensities of the transmitted light beams detected at the light-receiving section 6A are gradually increased. This is a second measuring area.

When the cuff pressure is further increased so as to exceed the arterial blood pressure, all the blood is eliminated, leaving only the tissue portion 7a. Thus, the luminous intensities of the light-receiving outputs change to an extremely small degree. This is a third measuring area.

If the oxygen saturations S in the second and the third measuring areas are measured by the oxygen saturation calculating means beat by beat, a judging means implemented by the CPU 1 determines whether or not the measured result is within the permissible range variance δ. Actually, a difference between the measured oxygen saturation S and the mean value K is calculated, and whether or not the calculated result is within the permissible range of variance δ is checked. By defining a sum of the mean value K and the permissible range of variance δ as a permissible range of variance δ', whether or not the measured oxygen saturation S is within the permissible range of variance δ' may be determined.

A signal component separating means separates a photoelectric plethysmograph of at least one of the wavelengths of the light-receiving signals obtained in the second and the third measuring areas. A blood pressure measuring means implemented by the CPU 1 measures the amplitude of the photoelectric plethysmograph, and if the judging means determines that the measured oxygen saturation S is within the permissible range of variance δ, then the mean blood pressure value Pm, the systolic blood pressure value Ps, and the diastolic blood pressure value Pd are measured from the amplitude of the photoelectric plethysmograph determined as being valid and the cuff pressure value. If the measured oxygen saturation S is determined to be out of the permissible range of variance δ, then the processing for treating the separated photoelectric plethysmograph as being invalid is performed instantly, thereby not allowing the CPU 1 to calculate the blood pressure value using such invalid photoelectric plethysmograph.

The blood pressure measurement based on the volume oscillometric method effected by the above procedure can invalidate measurements obtained when the subject is under sever vibration in the second measuring area or measurements obtained in the third measuring area in which the ac component consisting of external noise due to, e.g., vibration erroneously recognized as a pulse wave that has not been detected is detected. Therefore, more reliable measurement is possible.

On the other hand, when the cuff 4 is attached to a brachial arm of the subject, the transmitted light cannot be detected. Therefore, with the light-emitting section 5 and a light-receiving section 6B disposed equidistantly apart from each other on the same plane, reflected light after light beams emitted from the light-emitting section 5 have been extinguished by their transmission through the tissue 7 is detected at the light-receiving section 6B.

In this case, if the cuff pressure is linearly increased as shown in FIGS. 13(a), (b), then the optical path length D that corresponds to the distance between the light-emitting section 5 and the light-receiving section 6B is maintained constant. However, since the arterial blood 7b including pulsation and the venous blood 7c are being gradually eliminated, the luminous intensities of the reflected light beams detected at the light-receiving section 6B are on the gradual increase as the detected waveforms shown in FIGS. 10(c), (d) and FIGS. 11(a), (b). When the cuff pressure has exceeded the arterial blood pressure, all the blood is eliminated to leave only the tissue portion 7a. As a result, the luminous intensities of the reflected light beams change to an extremely small degree.

Thus, even in the method involving the detection of the reflected light, reliable blood pressure measurement can be made by following the above operation procedure.

A sphygmomanometer, which is the second embodiment of the invention, will be described in detail with reference to the accompanying drawings.

Figure 8:
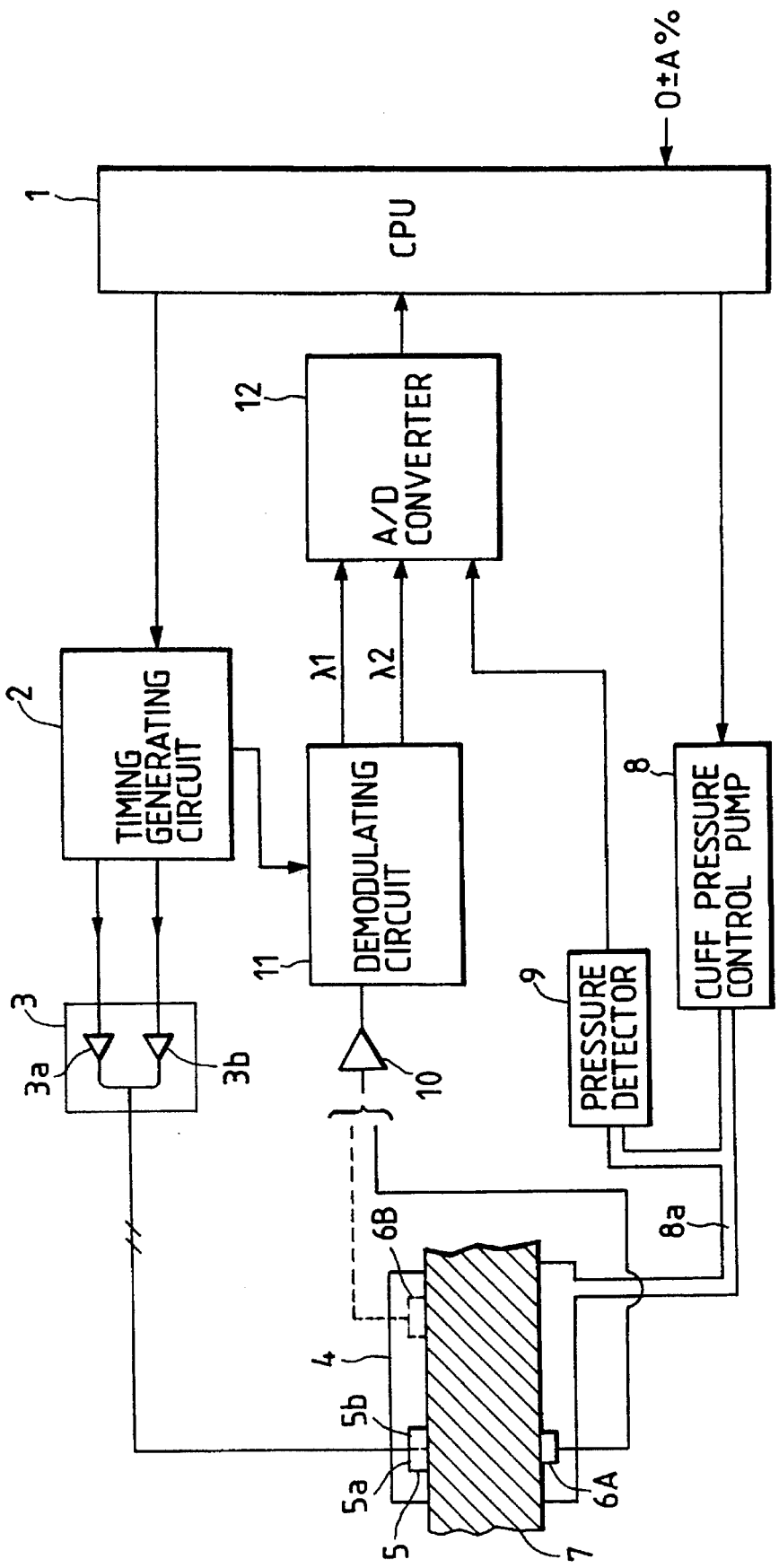
FIG. 8 is a block diagram showing a non-invasive blood pressure measurement device, which is a second embodiment of the invention.

The sphygmomanometer, which is the second embodiment, is shown in a block diagram of FIG. 8. In FIG. 8, the light-emitting section 5 and the light-receiving section 6A are mounted integrally with one another on the inner surface of the cuff 4 that is attached to a part of the body of a subject, e.g., a finger of his hand. The light-emitting section 5 is used to inject beams of light into the tissue 7 of the subject, and the light-receiving section 6A is disposed on a side opposite to the light-emitting section 5 so that the tissue 7 can be interposed therebetween. Here, it is assumed that the tissue 7 includes: the tissue portion 7a not containing blood; the arterial blood 7b, and the venous blood 7c (see FIG. 10 (a)). The light-receiving section 5 is formed of light-emitting elements for emitting beams of light of two different wavelengths, such as two light-emitting diodes 5a, 5b. Emitted from the respective light emitting diodes 5a, 5b are a beam of red light with a first wavelength $\lambda 1$ of 660 nm and a beam of the infrared light with a second wavelength $\lambda 2$ of 940 nm. Instead of using the two light-emitting didoes, filters of the respective colors disposed in front of light sources may be switched to emit the beams of light of two wavelengths. The light-receiving section 6A is formed of a light-receiving element such as a phototransistor, and detects the amounts of light transmitted after the light beams injected from the light-emitting section 5 have been transmitted through the tissue 7.

The cuff 4 is connected to a cuff pressure control pump 8 through an air tube 8a, the pump 8 including a drive circuit. The operation of increasing, decreasing, or releasing the cuff pressure can be performed by applying a control signal from the CPU 1 to the pump 8 that serves as a pressure applying means.

The cuff pressure to be applied to the tissue 7 through the cuff 4 is detected by a pressure detector 9, and the output of the pressure detector 9 is received by the CPU 1 after being converted into a digital signal at an A/D converter 12.

A timing generating circuit 2 under control of the CPU 1 applies not only pulse signals to buffers 3a, 3b of a driver circuit 3, but also timing signals to a demodulating circuit 11. The pulse signals determine timings for sequentially driving the respective light-emitting diodes 5a, 5b on a time-sharing basis. The timing signals serve to separate light-receiving signals from output signals of the light-receiving section 6A by the respective wavelengths $\lambda 1$, $\lambda 2$.

The respective buffers 3a, 3b sequentially amplify the received timing pulse signals and drive the respective light-emitting diodes 5a, 5b. Accordingly, the light-emitting diodes 5a, 5b sequentially inject beams of light with the first and the second wavelengths $\lambda 1$, $\lambda 2$ to the tissue 7.

The light-receiving section 6A detects the amounts of light transmitted after the beams of light injected from the light-emitting diodes 5a, 5b have been extinguished by their transmission through the tissue 7. These light-receiving signals are supplied to the demodulating circuit 11 after amplified by an input being amplifier 10.

The demodulating circuit 11 serving as a signal component separating means not only separates the light-receiving signals by the respective wavelengths $\lambda$, $\lambda 2$ from its input signals based on the timing signals, but also separates a dc component and a pulsatile component from each light-receiving signal. The respective signal components outputted from the demodulating circuit 11 are received by the CPU 1 after being converted into digital signals.

An allowance ($\pm A\%$), which is a coefficient used for calculating the permissible range of variance $\delta$ from the mean value K of the oxygen saturations S measured before applying pressure to the cuff can be input to the CPU 1 from an external unit.

Figure 9:
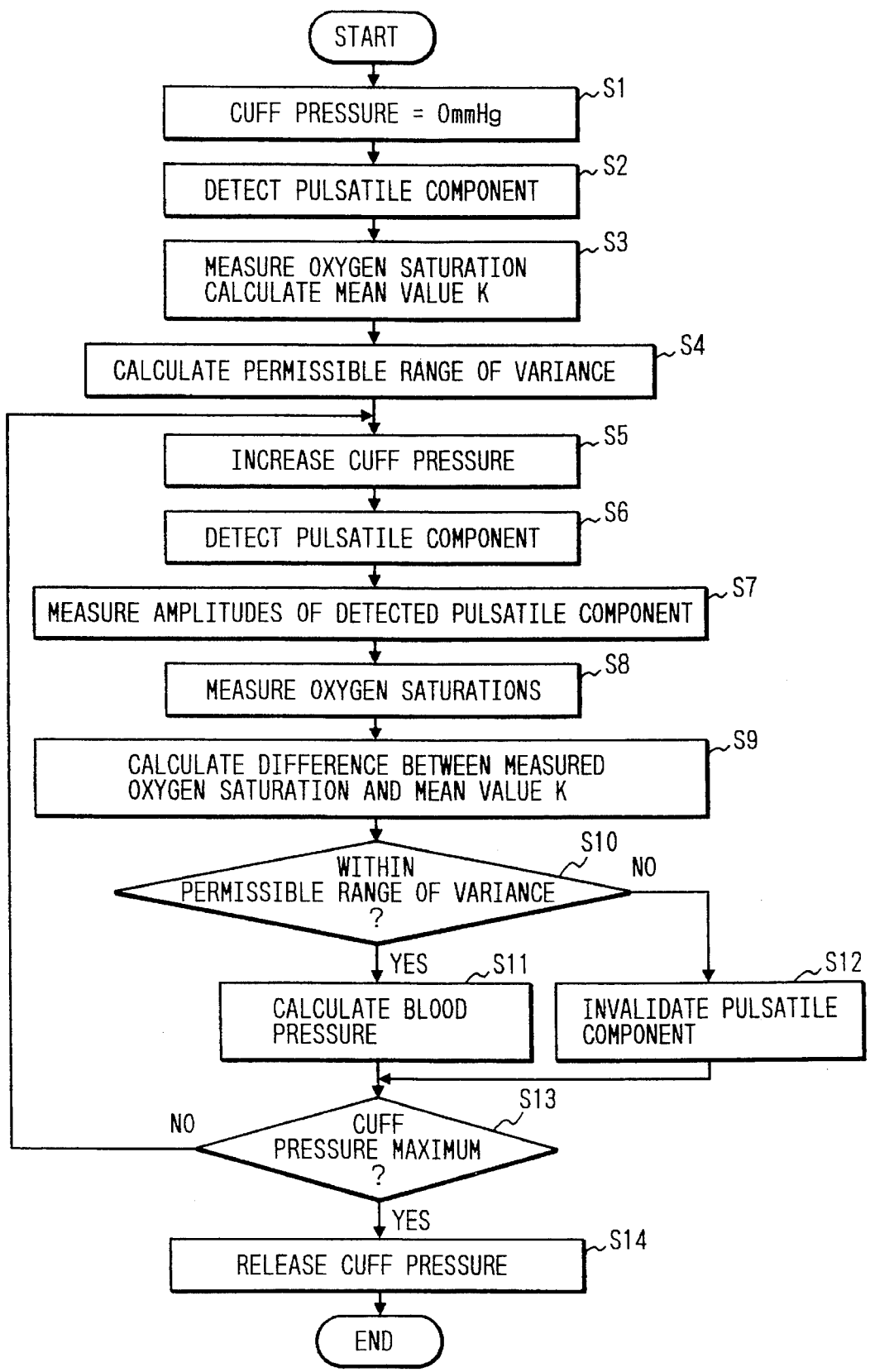
FIG. 9 is a flowchart showing an operation procedure of the sphygmomanometer of FIG. 8.

An operation of the thus constructed non-invasive blood pressure measurment device will be described next with reference to a flowchart of FIG. 9.

At the measurement start timing, the cuff is not pressured; i.e., the cuff pressure is maintained at 0 mmHg (Step S1). Under this condition, beams of light of the respective wavelengths $\lambda 1$, $\lambda 2$ are sequentially injected into the tissue 7 from the light-emitting diodes 5a, 5b of the light-emitting section 5, and the amounts of light transmitted are detected at the light-receiving section 6A. From each signal outputted from the light-receiving section 6A a dc component are and a pulsatile component separated, and these components are received by the CPU 1 (Step S2). The CPU 1 processes the input signals based on the above-mentioned operation procedure to measure the oxygen saturation S beat by beat, and calculate a mean value K of the measured oxygen saturations S (Step S3). The CPU 1 further calculates the permissble range of variance $\delta$ by multiplying the mean value K by the allowance ($\pm A\%$) (Step S4).

Then, the CPU 1 outputs a pressure increase control signal to the cuff pressure control pump 8. Accordingly, the pressure of the cuff 4 is linearly increased by the pump 8 (Step S5). In the course of increasing the cuff pressure, the operation similar to Step S2 is performed, so that the dc components and the pulsatile components separated from the light-receiving signals by the respective wave lengths $\lambda 1$, $\lambda 2$ are received by the CPU 1 (Step S6). The CPU 1 measures not only the amplitudes of the detected pulsatile components, i.e., photoelectric plethsmograph signals, but also the oxygen saturations S (Steps S7 and S8).

Further, the CPU 1 calculates a difference between the measured oxygen saturation S and the mean value K obtained in Step S3, and determines whether or not such difference is within the permissble range of variance $\delta$ (Steps S9 and S10). If the difference is judged to be within the permissble range of variance $\delta$, Step S11 will be executed. On the other hand, if the difference is determined to be out of the permissble range of variance $\delta$, due to noise caused by vibration or movement of the body, processing branches to step S12, for invalidating the detected photoelectric plethysmograph signal immediately.

Whether or not the cuff pressure has reached a set maximum value, e.g., 180 mmHg is determined in Step S13. If the maximum cuff pressure has not been reached, the processing is repeated from Step S5.

By a series of processing steps, the mean blood pressure value Pm, the systolic blood pressure value Ps, and the diastolic blood pressure value Pd of the subject are calculated from the amplitude of the valid photoelectric plethysmograph signal and the cuff pressure value every pulse in Step S11.

If it is determined that the cuff pressure has reached the maximum blood pressure in Step S13, then the cuff pressure is released to terminate the measurement (Step S14).

More reliable measurement may be achieved if blood pressure is measured again in the course of linearly decreasing the cuff pressure by sending a pressure decrease control signal to the cuff pressure control pump 8 after the cuff pressure has reached the maximum blood pressure.

By measuring blood pressure based on the volume oscillometric method while performing the above-mentioned processing, the sphygmomanometer of the invention can eliminate measurements in the third measuring area (see FIG. 11(c)) in which the measured oxygen saturation S differs markedly from the correct value as a result of erroneously recognizing a non-pulse noise component as a pulse, the noise component being caused by vibration or the like. The sphygmomanometer of the invention can also eliminate a measured value if such measured value is obtained from a large noise component out of the allowable range having been temporarily picked up in the second measuring area in which a pulse is detected; the S/N ratio is relatively large; and the oxygen saturations S are less erratic. Therefore, highly reliable measurement is possible.

Now, an embodiment in which measurement is made by attaching the cuff 4 to a brachial arm of the subject will be described. In this embodiment, the light-emitting section 5 and the light-receiving section 6B are mounted on the inner surface of the cuff 4 so as to be separated from each other by a predetermined distance as shown by a broken line in FIG. 8. The predetermined distance is the optical path length D between the light-emitting section 5 and the light-receiving section 6B.

In this case, the respective light-emitting diodes 5a, 5b of the light-emitting section 5 sequentially inject beams of light of two wavelengths λ1, λ2 into the tissue 7. The amounts of light reflected after the beams of light have been extinguished by their transmission through the tissue 7 are detected by the light-receiving section 6B. A measurement procedure in this case is as shown by a flowchart of FIG. 2.

As described above, according to the second embodiment of the invention, in a measuring environment involving vibration or movement of the body for which it is difficult to measure blood pressure by the conventional volume oscillometric method, reliable blood pressure measurement can be effected on a subject.

Accordingly, the invention can improve reliability of blood pressure measurement in ambulances, which have heretofore imposed problems, thereby contributing to the improvement of emergency medical treatment.

What is claimed is:

1. A non-invasive blood pressure measurement device comprising:

a cuff configured to be attached to a body part of a subject;

a pressure detector operatively connected to said cuff for detecting a cuff pressure applied to the body part by the cuff and outputting a detection output;

pressure applying means for applying pressure to the cuff in response to an input pressure increase control signal and for dropping the cuff pressure in response to an input pressure decrease control signal;

a light-emitting member for injecting beams of light of two different wavelengths, one being a beam of red light and the other being a beam of infrared light, into the body part of the subject to which pressure is applied by said cuff;

a light-receiving member for detecting one of amounts of light transmitted and amounts of light reflected of the beams of light injected into the body part from said light-emitting member, and thereby outputting light-receiving signals for the two different wavelengths;

signal component separating means operatively connected to said light-receiving member for separating a dc component and a pulsatile component from each of the light-receiving signals of the respective wavelengths obtained from said light-receiving member;

oxygen saturation calculating means for calculating a ratio of a pulsation component in absorption of one wavelength due to arterial blood flow to that of the other wavelength from the dc components and the pulsatile components of the respective wavelengths obtained from said signal component separating means, and for calculating an oxygen saturation from the ratio;

permissible range of variance calculating means for obtaining a mean value of oxygen saturation measurements of the subject before said pressure applying means applies pressure to the cuff, and for calculating a permissible range of variance from the mean value, the oxygen saturation measurements being obtained from said oxygen saturation calculating means;

cuff pressure control means for outputting the pressure increase control signal to said pressure applying means while receiving the detection output from said pressure detector, and for outputting the pressure decrease control signals, for dropping the once increased cuff pressure, to said pressure applying means, after the permissible range of variance has been obtained;

determining means for determining whether or not an oxygen saturation obtained in the course of increasing or decreasing the cuff pressure is within the permissible range of variance and for outputting a determination result; and blood pressure measuring means for selecting, based on the determination result output by said determining means, a valid pulse wave signal from the pulsatile components obtained by said signal component separating means in the course of increasing or decreasing the cuff pressure and for calculating a blood pressure value of the subject by a volume oscillometric method from an amplitude of the valid pulse wave signal and the detection output obtained from said pressure detector.

2. A method for measuring blood pressure non-invasively, the method comprising the steps of:

injecting beams of light of two different wavelengths, one being a beam of red light and the other being a beam of infrared light, into a body part of a subject to which a cuff is attached;

detecting one of amounts of light transmitted and amounts of light reflected of the beams of light injected into the body part and outputting, for each of the two wavelengths, a resultant light-receiving signal;

separating a dc component and a pulsatile component from each of the light-receiving signals of the respective wavelengths;

calculating a ratio of a pulsation component in absorption of one wavelength due to arterial blood flow to that of the other wavelength from the dc components and the pulsatile components of the respective wavelengths;

calculating an oxygen saturation from the ratio;

obtaining a mean value of oxygen saturation measurement of the subject before applying pressure to the cuff;

calculating a permissible range of variance from the mean value;

increasing pressure to the cuff while detecting the cuff pressure, or decreasing the cuff pressure while detecting the cuff pressure, after the permissible range of variance is calculated;

determining whether or not an oxygen saturation obtained in the course of increasing or decreasing the cuff pressure is within the permissible range of variance and then outputting a determination result; and selecting, based on the determination result, a valid pulse wave signal from the pulsatile components in the course of increasing or decreasing the cuff pressure;

calculating a blood pressure value of the subject by a volume oscillometric method from an amplitude of the valid pulse wave signal and the detected cuff pressure.

* * * * *